United States Patent [19]

Riggsbee

[11] Patent Number: 4,767,654

[45] Date of Patent: Aug. 30, 1988

[54] DETACHABLE COUPON LABEL

[75] Inventor: James H. Riggsbee, North Augusta, S.C.

[73] Assignee: United Merchants & Manufacturers, Inc., New York, N.Y.

[21] Appl. No.: 788,787

[22] Filed: Oct. 18, 1985

[51] Int. Cl.[4] .......................... A61F 13/02; C09J 7/02

[52] U.S. Cl. .......................................... 428/40; 428/42; 428/352; 428/914; 40/310; 206/390; 493/220

[58] Field of Search .................. 40/310, 312; 206/390; 428/40, 42, 352, 914; 493/220

[56] References Cited

U.S. PATENT DOCUMENTS

| | | | |
|---|---|---|---|
| 3,994,089 | 11/1976 | Schwartz | 40/310 |
| 4,060,168 | 11/1977 | Romagnoli | 206/214 |
| 4,281,762 | 8/1981 | Hattemer | 206/390 |
| 4,345,393 | 8/1982 | Price et al. | 40/312 |
| 4,359,358 | 11/1982 | Hattemer | 156/248 |
| 4,363,685 | 12/1982 | White | 156/212 |
| 4,398,985 | 8/1983 | Eagon | 156/233 |
| 4,479,838 | 10/1984 | Dunsirn et al. | 156/247 |
| 4,526,405 | 7/1985 | Hattemer | 283/81 |
| 4,528,055 | 7/1985 | Hattemer | 156/247 |
| 4,537,586 | 8/1985 | Gale et al. | 493/220 |
| 4,544,590 | 10/1985 | Egan | 428/40 |
| 4,545,781 | 10/1985 | Carl et al. | 493/220 |

*Primary Examiner*—John E. Kittle
*Assistant Examiner*—Patrick J. Ryan
*Attorney, Agent, or Firm*—Kenyon & Kenyon

[57] ABSTRACT

A removable coupon label structure comprising a casting substrate; a resin film attached to the casting substrate to form a composite web; and an adhesive situated on the resin film side of the composite web whereby the composite web is suitable for mounting on a backing substance and the casting substrate may be separated from the resin film at a desired release force of about 10 to about 100 grams per inch width.

18 Claims, 1 Drawing Sheet

DETACHABLE COUPON LABEL

This invention relates to an improved composite detachable coupon label structure appropriate for attaching to packages or containers which permits the coupon label to be readily detached without leaving a tacky residue and without the use of a release substance.

In the production and merchandising of goods, it is often desirable to make use of removable coupons or labels contained on containers or packages that function as redeemable retail coupons, inventory control labels and the like. In these functions, it is desirable and often necessary that the coupon label not be prone to premature detachment during shipping and handling, yet be readily removable. In the case of instantly redeemable in-store coupons, for instance, the coupon is removed from a container by the buyer at the time of purchase and then redeemed for a discount on the product at the point of purchase. For this particular use, the coupon must be readily removable by the consumer from the container or package for redemption, yet be bound securely enough so that premature detachment does not occur during shipping and handling.

Attempts have been made to use adhesives to keep the coupon label securely attached to the package or container but the adhesive often makes removal of the coupon difficult due to the strength of the adhesive. Moreover, adhesives tend to leave an undesirable tacky residue on both the coupon label and package or container. Consequently, these problems often discourage producers and merchandizers from utilizing this effective form of product promotion. These types of problems, of course, exist not only with respect to instant redemption or other retail coupons, but also when it is desired to make use of removable coupons, tags or labels for such purposes as inventory control tags and tamper indicating labels. In light of the advantages to be gained from the use of removable coupon labels, numerous previous attempts have been made to provide detachable coupons or labels that avoid the problems discussed hereinabove.

U.S. Pat. No. 3,336,862 describes a structure in which a tag having a film of pressure-sensitive adhesive on one surface thereof is separated from the pressure-sensitive adhesive coating on the label by a sheet having adhesive release surfaces on opposite sides thereof. Thus, the patent provides for a tag-label structure in which the label can be readily removed from the tag with all or a portion of its adhesive surface exposed for the purpose of affixing it directly to an article.

U.S. Pat. Nos. 4,359,358 and 4,281,762 disclose a composite structure providing a removable in-store coupon. The structures contain a base sheet with adhesive for securing the sheet to a container and a top sheet comprising, in part, a removable in-store coupon. The top sheet has side portions permanently secured to the underlying base sheet with an adhesive and a central coupon free of said base sheet and detachably secured to and between said portions. Perforations between the central coupon and the side portions permit detachment of the central coupon from the side portions which act to attach the central coupon to the container.

U.S. Pat. No. 4,363,685 and Reissue Pat. No. 30,958 disclose a package label composed of one section permanently attached to an object with a thermosetting adhesive and a second section which is separably connected to the first section and has the same adhesive on its back. Superimposed on a portion of the thermosensitive adhesive is a strip of pressure sensitive adhesive and a suitable release liner. This section of the label is separated from the first, the release liner removed and the label mounted on an object. The disclosure relates particularly to dispensing and recording labels for pharmaceutical products.

U.S. Pat. No. 4,398,985 to Eagon describes a laminated construction useful for tags, labels and stickers, in which a self-detackifying laminate is prepared in which a face stock sheet is first coated with a layer of a non-silicone release polymer. A non-silicone polymer film is then coated onto the release polymer, and an adhesive coated on a release liner is then applied to the polymer film. The release liner can then be removed and the adhesive bonds the construction to a package. Removal of the face stock, e.g., as a coupon, will leave behind the polymer film to cover the adhesive.

U.S. Pat. No. 4,479,838 describes a coupon structure comprising a top sheet (or coupon) releasably adhered to the upper side of a base sheet by a substantially transparent layer of dry residue adhesive. To the lower side of the base sheet is applied a second adhesive for permanently attaching the construction to a package, for example. The nature of the first adhesive is such that when the top sheet (or coupon) is removed from the base sheet, a dry, substantially transparent, non-tacky residue is exposed.

Thus, there are an abundance of coupon label arrangements known to those skilled in the art. It has heretofore been widely believed, however, that an effective detachable coupon label had to employ an adhesive to ensure that the coupon or label did not prematurely detach from the carton or container. In a case where an adhesive is not employed for this purpose, in the above-described U.S. Pat. No. 4,398,985 for instance, it has been necessary to make use of a release polymer between the face stock, e.g. coupon, and a non-silicone polymer film to ensure that the face stock or coupon can be readily removed from the carton or container.

Accordingly, there exists a need for a coupon label that will securely adhere to packaging without the use of an undesirable tacky adhesive and which can be readily removed without the use of a release substance.

SUMMARY OF THE INVENTION

It is an object of the invention to provide a coupon label that securely adheres to packaging;

It is another object of the invention to provide a coupon label that securely adheres to packaging yet can be readily removed therefrom without the use of a release substance;

It is another object of the invention to provide a coupon label structure that leaves no tacky residue on the coupon or package once the coupon portion has been removed from the package;

It is yet another object of the invention to provide a composite coupon label stock with a maximum of printing space;

It is another object of the invention to provide an improved in-store coupon label stock.

It is another object of the invention to provide a removable coupon label structure that can be applied over existing packaging.

These and other objects are achieved by a removable coupon label structure comprising a casting substrate; a resin film attached to the casting substrate to form a composite web; an adhesive situated on the the extruded resin film side of the composite web whereby the composite web is suitable for mounting on a backing substance and the casting substrate may be separated from the resin film at a desired release force.

The resin film may be extruded onto the casting substrate in melt form or laminated thereon in solid form. The amount of release pressure needed to separate the casting substrate from the resin film has been determined to be in the range of about 10 to about 100 grams-/inch width. The resin film is a thermoplastic resin, preferably one such as polyethylene, polypropylene, polyester, polyurethane, polyacrylate, polycarbonate or surlyn. The casting substrate itself may be paper or a thermoplastic film such as polyester.

The invention also contemplates a method of preparation of a removable coupon label which comprises providing a casting substrate; attaching a resin film onto one side of said casting substrate to form a composite web under conditions appropriate to achieving a desired release force to separate the casting substrate from the resin film; applying an adhesive to the resin film side of the composite web; and applying the adhesive coated composite web to a backing sheet or package whereby the casting substrate may be detached from the resin film at a desired release force.

DETAILED DESCRIPTION OF THE INVENTION

Figure 1:
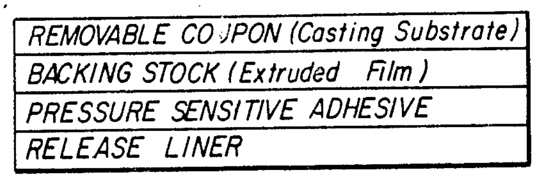
FIG. 1 is a block diagram of the coupon label structure according to the invention.

In accordance with the invention, it has surprisingly been discovered that a coupon or label can be securely attached to a package or container without an adhesive and can be readily detached from the package or container without the use of a release substance in contact with the coupon or label. Thus, the invention relates to an improved detachable coupon label and methods of making same and has application in areas such as store redemption retail coupons, inventory control tags, tamper indicating labels, etc. Moreover, the coupon label according to the invention can be applied over existing packaging, thus eliminating the need for special primary labels.

When a coupon label is applied onto existing packaging, it is imperative that the coupon label be bound securely enough so that premature detachment does not occur during shipping and handling, yet not be bound so securely that the coupon label is not readily removable. The novel coupon label according to the invention achieves these goals without the use of an adhesive to securely attach the coupon or a release substance to facilitate the detachment of the coupon label from the container or package. Because the coupon label according to the invention does not utilize an adhesive to adhere the detachable coupon label to the remainder of the coupon label structure, an additional advantage is achieved by the invention in that handling of both the coupon label and package is facilitated after the coupon label is removed since no tacky residue is present.

The coupon label according to the invention comprises a composite web of a resin film or base sheet attached to a casting substrate or top sheet without making use of a release substance. The casting substrate or top sheet, in the preferred embodiment, acts as the removable coupon label. A pressure sensitive or other adhesive is applied onto the exposed resin film side of the composite web, and is used to firmly attach the composite web to a backing sheet or to the package or container itself. The backing sheet may be applied to any package, container or substance to which the composite web may be adhered using any type of adhesive suitable for attaching the composite web directly to the package or container.

The casting substrate or top sheet, e.g., coupon, may be composed of any substance that is capable of forming the composite web with the resin film to achieve the desired degree of London or dispersion force necessary to maintain the casting substrate on the resin film at the desired release force. London or disperson force, as defined herein, is the force of attraction created between the casting substrate and resin film. A certain desired release force is needed to overcome the London or dispersion force created in order to separate the casting substrate from the resin film.

Preferably, the casting substrate is paper or a thermoplastic film such as polyester, or a combination of such materials, provided that the casting substrate be in solid form at the melt temperature of the resin film when the resin film is extruded thereon. Thus, for example, it is possible to extrude a low density polyethylene resin onto a polyester film to achieve the composite web only after the polyester film is in the form of a solid. Printing may be applied to either or both sides of the casting substrate depending on the type of material utilized.

The resin film or base sheet, which is attached onto one side of the casting substrate or top sheet, is a thermoplastic resin such as high density polyethylene, low density polyethylene, polypropylene, polyester, polyurethane, polyacrylate, polycarbonate and surlyn. Depending on the conditions and type of resin used, the resin film may be clear, translucent or opaque. When the resin film is clear, it is possible to transmit any desired message on a backing sheet or on the container or package once the coupon or label has been removed.

The resin film may be applied to the casting substrate in either a solid or liquid state. Preferably, the resin film is extruded in a melt or liquid state onto one side of the the casting substrate under conditions appropriate to achieving a London or dispersion force that permits the casting substrate to be stripped from the resin film at a desired release force. The thermoplastic resin in melt or liquid form may be extruded from a die into the nip of two rolls where it contacts and bonds to a casting substrate under elevated conditions of temperature and pressure.

In another embodiment of the invention, a preformed solid resin film may be laminated to the casting substrate under the conditions appropriate to achieving the desired release force.

Composite webs may be employed which require a very small release force to strip the casting substrate from the resin film, while other composite webs require large release forces. Release forces in between are all possible, depending on the strength of the London or dispersion force established between the casting substrate and resin film. The release force needed to overcome the London or dispersion force at the casting substrate/resin film interface, however, must be within a certain range for proper functioning of the coupon label. Thus, a low release force could possibly result in premature separation, while a high release force may create difficulties in peeling away the coupon label. In this regard, it has been found that the coupon label according to the invention requires a release force ranging from about 10 to about 100 grams per inch width to effectuate proper separation of the casting substrate from the resin film, with a preferred range being about 20 to about 60 grams per inch width. A composite web composed of a casting substrate and an extruded resin film satisfying the requirement of the effective release force described herein is available from Schoeller Technical Papers, Pulaski, N.Y.

The achievement of the desired London or dispersion force depends upon the control of certain factors such as the temperature of the resin film melt when contacting the casting substrate, the pressure at the point of lamination of the resin film and casting substrate, the Corona discharge treatment of the casting substrate's surface prior to lamination, and the oxidative etching of the casting substrate's surface prior to lamination. The creation of the composite web, for example, requires the application of an elevated temperature and pressure as demonstrated in examples 5 and 6 herein.

The composite web may be secured to a backing sheet or directly to a package by means of an adhesive, preferably a pressure sensitive adhesive. The composite web may first be secured to a backing sheet through the use of a pressure sensitive or other adhesive, and the entire coupon label structure, the composite web attached to a backing sheet, may be firmly adhered to the package or container. In the alternative, the composite web may be adhered directly to the package or container without the use of a backing sheet. In this embodiment, the adhesive is applied directly to the casting substrate or to the resin film side of the composite web, which side is then adhered to the container or package. The side to which the adhesive is not applied may then be readily detached by applying the appropriate release force.

In the preferred embodiment, the casting substrate or top sheet, e.g., coupon, may be peeled away using the appropriate release force leaving the resin film attached to the packaging or backing sheet. When a transparent resin film is employed, the original package printing, or any message or coupon contained on the backing sheet, is visible after the casting substrate is removed.

In another embodiment of the invention, a message or second coupon may be back printed on the resin film side of the composite web prior to the application of the adhesive. After the composite web is attached to the package or backing sheet, removal of the casting substrate, e.g., coupon, would then expose the back printed resin film bonded to the package or backing sheet thereby revealing a desired message.

To adhere the composite web to the backing sheet or package, it is possible to directly apply adhesive to the resin film portion of the composite web or, in the alternative, the adhesive can be transfer coated onto the resin film side of the composite web by known industry techniques. It is preferable to apply the adhesive by means of transfer coating, since direct coating of the adhesive may effect the integrity of the London or dispersion force between the casting substrate and resin film. In the process of transfer coating, the adhesive is cast onto a release liner which is then joined to the resin film side of the composite web. When ready to apply the composite web to the backing sheet or package, the release liner is pulled away enabling the application of the composite web to the backing sheet or package. The force required to pull the release liner from the adhesive layer should be less than the force required to remove the casting substrate or coupon from the resin film so as to avoid premature detachment of the casting substrate from the resin film. Pressure sensitive adhesives are preferred, but other types of pre-coating adhesives suitable for use in the invention include thermosetting, thermoplastic or water activated adhesives.

The composite web may be converted into a removable coupon label containing some type of printed message by subjecting the composite web either in roll or sheet form through methods of operation known in the industry for inline printing and die cutting. Labelling machines well known to the industry may then be used to apply the coupon label to containers or packages.

With reference to the figures, FIG. 1 displays the basic arrangement of the preferred embodiment of the invention. The removable coupon or casting substrate is attached to the extruded resin film at a desired release force. The extruded resin film is attached to a release liner by means of an adhesive, preferably a pressure sensitive adhesive. Once the release liner is removed, the composite web may be attached to a backing sheet which is attached to a package or container, or to the package or container itself.

Figure 2:
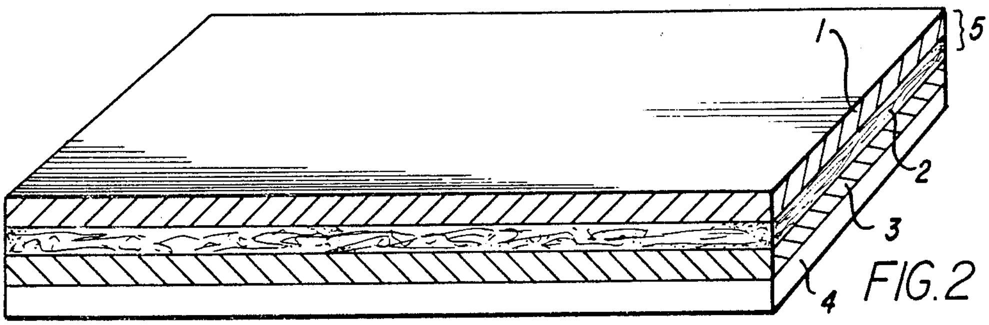
FIG. 2 is a perspective view of the coupon label according to the invention.

FIG. 2 is a perspective view of the coupon label according to the invention, with composite web 5 made up of casting substrate or coupon 1 and extruded film 2 attached to a backing sheet or package 4 by means of pressure sensitive adhesive 3.

Figure 3:
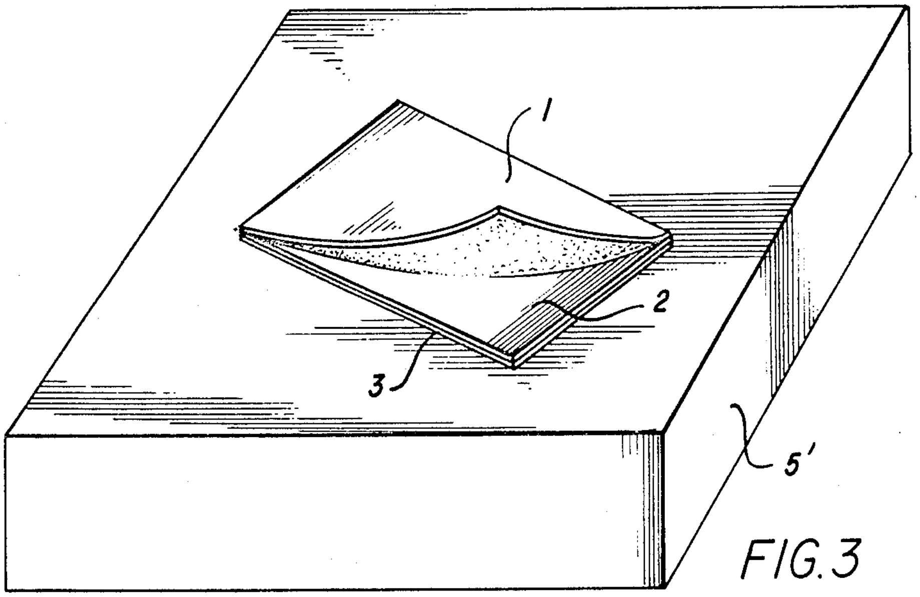
FIG. 3 is a perspective view of a container to which is attached a coupon label according to the invention with the coupon portion partially detached.

FIG. 3 illustrates the removal at a desired release force of the casting substrate on coupon 1 from a container 5, with the extruded film or base sheet 2 remaining secured to the container 5' by means of adhesive 3. When the extruded film or base sheet 2 is composed of a clear material, container 5 remains visible through the extruded film 2 and the adhesive 3.

The invention is described in further detail by the following examples.

EXAMPLE 1

A pressure sensitive adhesive latex (Valtac 35 from Valchem, a terpolymer of butyl acrylate/2-ethylhexyl acrylate/vinyl acetate) was coated on a silicone coated paper release liner with a wire wound rod. The coating was dried in an air circulating oven for five minutes at 158 degrees F. The dry adhesive coating weight was 14.5 lb./3,000 sq. ft. ream.

The adhesive coating was then laminated to a strippable 1.3 mil low density polyethylene (LDPE) film cast on 4 mil bleached kraft available from Schoeller Technical Papers Pulaski, N.Y. The release value of the LDPE film from the bleached kraft was 30 gm/inch width when measured on an Instron Tester at a rate of 12 inches/minute and an angle of 180 degrees. The release value of the silicone coated release liner from the pressure sensitive adhesive layer was 14 gm/inch width when peeled at a rate of 12 inches/minute and an angle of 180 degrees.

To demonstrate the use of above described construction as a coupon label, the release liner was first peeled away from the adhesive layer. The adhesive coated composite was applied to a corrugated board. The 4 mil bleached kraft was peeled away as a coupon, leaving behind on the board the adhesive coated 1.3 mil LDPE film.

EXAMPLE 2

An adhesive coating was prepared as described in Example 1. This coating was then laminated to the bleached kraft paper side of the LDPE/bleached kraft composite web from Example 1. The release liner, attached to the bleached kraft paper, was removed and the adhesive layer used to bond the composite web to a corrugated board. The 1.3 mil LDPE was peeled away as a coupon, leaving behind the bleached kraft paper adhered to the corrugated board by the pressure sensitive adhesive.

EXAMPLE 3

Coupon labels were constructed in a manner similar to those of Example 1 and 2 using Valtac 35 adhesive and a strippable 3.5 mil polyester film cast on a 4.5 mil bleached kraft paper from Schoeller Technical Papers. The release value of the polyester film from the kraft paper was 58 gm/inch width as measured by the method in Example 1.

EXAMPLE 4

Constructions suitable for coupon label stock were prepared according to the methods of Example 1 and 2 with the following materials from Schoeller Technical Papers:

| Strippable Extruded Resin Film | Casting Substrate |
|---|---|
| (1) 1 mil LDPE | 1 mil polyester |
| (2) 1 mil LDPE | 6 pt. paper |
| (3) 1 mil LDPE | 10 pt. paper |
| (4) 1 mil LDPE | 7 mil polypropylene |

These strippable films had release values of 20–30 gm/inch width when measured as in Example 1.

EXAMPLE 5

The lamination of resin films to casting substrates under elevated temperature and pressure was demonstrated as an alternative to the extruded strippable films of Examples 1–4. The release value of a film from a substrate could be controlled by the proper choice of temperature, pressure and time of lamination.

A 4.5 mil high density polyethylene (HDPE) film was laminated to a 57 lb/3,000 sq. ft. ream of white paper using a Carver press with heated platens. The film was placed on a siliconized kraft release liner to protect the film from the heated plate, then covered with the white paper. The system was placed in the press having 240° F. upper platen ($T_1$) and 195° F. lower platen ($T_2$). A pressure of 140 lb/sq. in. was applied for various times. In the following table are reported release values for the various lamination times measured in accordance with Example 1:

| Sample | Time (Sec) | Release (gm/in width) |
|---|---|---|
| 1 | 5 | 18 |
| 2 | 15 | 66 |
| 3 | 30 | 73 |
| 4 | 60 | 87 |

EXAMPLE 6

Using the method of Example 5, six strippable film composites were prepared with various release values:

| SAMPLE FILM | SUBSTRATE | $T_1/T_2$ (°F.) | TIME (SEC) | PRESSURE (PSI) | RELEASE (GM/IN) |
|---|---|---|---|---|---|
| 1. 1.5 MIL LDPE | 2 Mil Polyester | 245/200 | 30 | 140 | 10 |
| 2. 1.5 MIL LDPE | 2 Mil Polyester | 245/200 | 30 | 220 | 16 |
| 3. 1.5 MIL LDPE | 2 Mil Polyester | 220/195 | 60 | 220 | 7 |
| 4. 1.5 MIL LDPE | 60 LB. Paper | 245/200 | 30 | 140 | 41 |
| 5. 4.0 MIL HDPE | 60 LB. Paper | 245/200 | 15 | 140 | 46 |
| 6. 4.0 MIL HDPE | 60 LB. Paper | 220/195 | 30 | 140 | 18 |

While there have been described what are presently believed to be preferred embodiments of the invention, it will be apparent to a person skilled in the art that numerous changes can be made in the ingredients, conditions and proportions set forth in the foregoing embodiments without departing from the invention as described herein and as defined in the appended claims.

What is claimed is:

1. A removable coupon label structure comprising (a) a casting substrate;

(b) a thermoplastic resin film attached to the casting substrate by means comprising attraction forces between the resin film and casting substrate to form a composite web; and (c) an adhesive situated on the resin film side of the composite web, opposite the casting substrate, whereby the composite web is suitable for mounting on a backing substance and the casting substrate may be separated from the resin film at a release force that effectuates such separation.

2. The removable coupon label structure according to claim 1 wherein the casting substrate is chosen from the group consisting of paper and polyester.

3. The removable coupon label structure according to claim 1, wherein the thermoplastic resin is selected from the group consisting of polyethylene, polypropylene, polyester, polyurethane, polyacrylate, polycarbonate and surlyn.

4. The removable coupon label structure according to claim 1 wherein the release force is about 10 to about 100 grams per inch width.

5. The removable coupon label structure according to claim 1, wherein the release force is about 20 to about 60 grams per inch width.

6. The removable coupon label according to claim 1 wherein the adhesive is selected from the group consisting of a pressure sensitive adhesive, a water activating adhesive, and a thermoplastic adhesive.

7. The removable coupon label structure according to claim 1, wherein the resin film is extruded in melt form onto the casting substrate.

8. A removable coupon label structure comprising (a) a casting substrate;

(b) a thermoplastic resin film attached to the casting substrate by means comprising London or dispersion forces to form a composite web; and (c) an adhesive situated on the resin film side of the composite web opposite the casting substrate, whereby the composite web is suitable for mounting on a backing substance and the casting substrate may be separated from the resin film at a release force of about 10 to about 100 grams per inch width.

9. The removable coupon label structure according to claim 8, wherein the casting substrate is chosen from the group consisting of paper and polyester and the resin film is selected from the group consisting of polyethylene, polypropylene, polyester, polyurethane, polyacrylate, polycarbonate and surlyn.

10. The removable coupon label structure according to claim 8, wherein the release force is between about 20 to about 60 grams per inch width.

11. The removable coupon label structure according to claim 8, wherein the resin film is extruded onto the casting substrate.

12. The removable coupon label structure according to claim 8, wherein the resin film is a solid which is laminated to the casting substrate.

13. The removable coupon label structure according to claim 8, wherein the resin film is transparent such that once the casting substrate is removed, a message contained on the backing substrate is evident.

14. The removable coupon label structure according to claim 8, wherein a message is back printed on the resin film side of the composite web prior to the application of the adhesive.

15. A process for the preparation of a removable coupon label which comprises:

(a) providing a casting substrate;

(b) attaching a thermoplastic resin film onto one side of said casting substrate to form a composite web by means comprising attraction forces between the resin film and casting substrate under conditions that permit the separation of the casting substrate from the resin film upon the application of a release force;

(c) applying an adhesive to the resin film side of the composite web opposite the casting substrate; and (d) applying the adhesive coated composite web to a backing sheet or package whereby the casting substrate may be separated from the resin film upon application of the release force.

16. The process according to claim 15, wherein the resin film is extruded in melt form onto the casting substrate and the release force is about 10 to about 100 grams per inch width.

17. The process according to claim 15, wherein the resin film is laminated in a solid form onto the casting substrate and the release force is about 10 to about 100 grams per inch width.

18. The process according to claim 15, wherein the casting substrate is selected from the group consisting of paper and polyester and the resin film is selected from the group consisting of polyethylene, polypropylene, polyester, polyurethane, polyacrylate, polycarbonate and surlyn.

* * * * *